United States Patent [19]

Danielson et al.

[11] Patent Number: 5,391,483
[45] Date of Patent: Feb. 21, 1995

[54] LIGAND ANALOGOS FOR IMMUNOASSAYS DERIVED FROM DICARBOXYLIC ACID OXIDATION PRODUCTS

[75] Inventors: Susan J. Danielson; Michael R. Detty, both of Rochester, N.Y.

[73] Assignee: Eastman Kodak Company, Rochester, N.Y.

[21] Appl. No.: 907,345

[22] Filed: Jul. 1, 1992

Related U.S. Application Data

[62] Division of Ser. No. 564,940, Jul. 27, 1990, abandoned.

[51] Int. Cl.⁶ .......................... C12Q 1/28; C12Q 1/26; C12Q 1/00; C07H 15/00
[52] U.S. Cl. .......................................... 435/28; 435/25; 435/4; 435/7.1; 435/7.5; 435/7.92; 435/7.94; 435/7.72; 436/527; 536/17.1; 424/1.73
[58] Field of Search ...................... 435/28, 7, 7.5, 7.92, 435/7.947.72, 25, 4, 7; 424/1.1, 9; 536/17.1

[56] References Cited

U.S. PATENT DOCUMENTS

| | | | |
|---|---|---|---|
| 3,850,752 | 11/1974 | Schuurs et al. | 424/12 |
| 3,875,011 | 4/1975 | Rubenstein et al. | 424/12 |
| 3,997,525 | 12/1976 | Guy | 536/7 |
| 4,184,037 | 1/1980 | Wilkinson | 536/7 |
| 4,279,992 | 7/1981 | Boguslaski et al. | 435/7.72 |
| 4,469,797 | 9/1984 | Albarella | 435/7 |
| 4,551,426 | 11/1985 | Freytag et al. | 435/793 |

FOREIGN PATENT DOCUMENTS

1060380  3/1989  Japan ............................. 435/188

OTHER PUBLICATIONS

*Oxidation and Reduction of Organic Compounds,* K. L. Rinehart, 1973, pp. 68–72 and 80–82.

Primary Examiner—Michael G. Wityshyn
Assistant Examiner—Louise N. Leary
Attorney, Agent, or Firm—John R. Everett

[57] ABSTRACT

What is disclosed is a ligand analog comprising a dicarboxylic acid oxidation product of a immunologically reactive mono-or a polysaccharide having vicinal diols, to which a label or a support is appended through an amide or thioester linkage.

5 Claims, 1 Drawing Sheet

LIGAND ANALOGOS FOR IMMUNOASSAYS DERIVED FROM DICARBOXYLIC ACID OXIDATION PRODUCTS

This is a Divisional of application Ser. No. 564,940, filed Jul. 27, 1990, now abandoned.

FIELD OF THE INVENTION

This invention relates to a dicarboxylic acid oxidation product of an immunologically reactive species-comprising mono- or a polysaccharide having vicinal diols to which a label or a support is appended through an amide linkage, and a process for its preparation and use in immunoassays.

BACKGROUND OF THE INVENTION

Immunoassays, which take advantage of natural immunological reactions, have found widespread use as analytical techniques in clinical chemistry. Because of the specificity of the reactions, they are particularly advantageous in quantifying biological analytes (called ligands herein) which include, for example, antibodies therapeutic drugs, narcotics, enzymes, hormones, proteins, etc.

In competitive binding assays, a labeled ligand analog (sometimes referred to as ligand analog herein) is placed in competition with the unlabeled ligand for reaction with a fixed amount of the appropriate binding material (called a receptor herein). Unknown concentrations of the ligand can be determined from the measured signal of either the bound or unbound (i.e. free) ligand analog. The reaction proceeds as follows:

ligand + ligand analog + receptor
⇌ ligand-receptor + ligand-analog receptor.

The traditional approach to the preparation of labeled ligand analogs for haptens such as steroids that contain carbohydrate residues with vicinal diols on the terminal monosaccharide residue, involves the oxidation of the terminal monosaccharide residue of steroids to a dialdehyde followed by attachment to amine residues of an enzyme label. The problem is that this approach has not generated satisfactory enzyme labeled ligand analogs for immunoassays. In such assays a substantial amount of the analog is not bound by antibody. Attempts to functionalize digoxigenin, the steroid component of digoxin, have met with limited success due to limited recognition of such functionalized material by the antibody. It would be desirable to have functionalized steroid derivatives that are easily bound to labels and that are recognized by antibodies for such steroids.

SUMMARY OF THE INVENTION

The present invention provides a ligand analog comprising a dicarboxylic acid oxidation product of an immunologically reactive mono- or a polysaccharide having vicinal diols, to which a label or a support is appended through an amide or thioester linkage.

The following structure is representative of the ligand analogs:

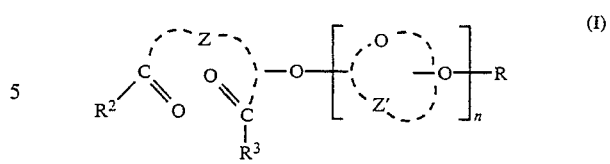

R is an immunologically reactive group devoid of vicinal diol, carboxylic acid, primary amine and sulfhydryl groups;

Z represents the residual atoms of a saccharide ring having dicarboxylic acid groups formed from the oxidation of the carbon atoms containing vicinal diol groups;

Z' represents the atoms necessary to complete a saccharide ring; and n is an integer from 0 to about 2,500.

$R^2$ and $R^3$ each independently represents a) $-OR^4$, $SR^4$, $-NR^4R^5$; or b) the residue of a label or support linked through an amino or sulfhydryl group to the carboxyl to which it is attached to form an amide (—NHCO—) or thioester

linking group;

$R^4$ and $R^5$ are each independently selected from hydrogen, lower alkyl of about 1 to 6 carbon atoms, or aryl of about 6 to 10 carbon atoms; provided at least one of $R^2$ and $R^3$ contains a label or support residue and the linkage between monosaccharide units is an α or β glycosidic bond.

The present invention also provides a method of making a ligand analog of the invention, comprising the steps of:

(a) providing a mono- or a polysaccharide having a group capable of specific binding with an immunologically reactive analyte (ligand) and two vicinal diols located on a terminal saccharide group;

(b) oxidizing the terminal saccharide at the vicinal diol portion with a mixture of periodic acid and chromium trioxide in an aqueous solution of a water-miscible organic solvent, to produce the dicarboxylic acid product; and (c) condensing the dicarboxylic acid product with a label or support containing an amino or sulfhydryl group. The support is preferably a polymer particle or membrane.

It is understood that this linking group can be part of a longer linking group on the label or support which is either inherent to the label or support, or is specifically provided on the label or support to facilitate the condensation in step (c). It is also understood that the carboxylic acid groups can be converted to reactive equivalents such as the acid halides, anhydride or ester, to facilitate the condensation step and that the linking groups alternatively could be first appended to the dicarboxylic acid oxidation product, then to the label or support.

We have observed improved immunoreactivity and dose response curves in immunoassays using the novel labeled ligand analogs (Structure I) of the present invention, particularly analogs that include the steroid derivatives of digoxin, digitoxin and ouabain.

DETAILS OF THE INVENTION

Figure 1:
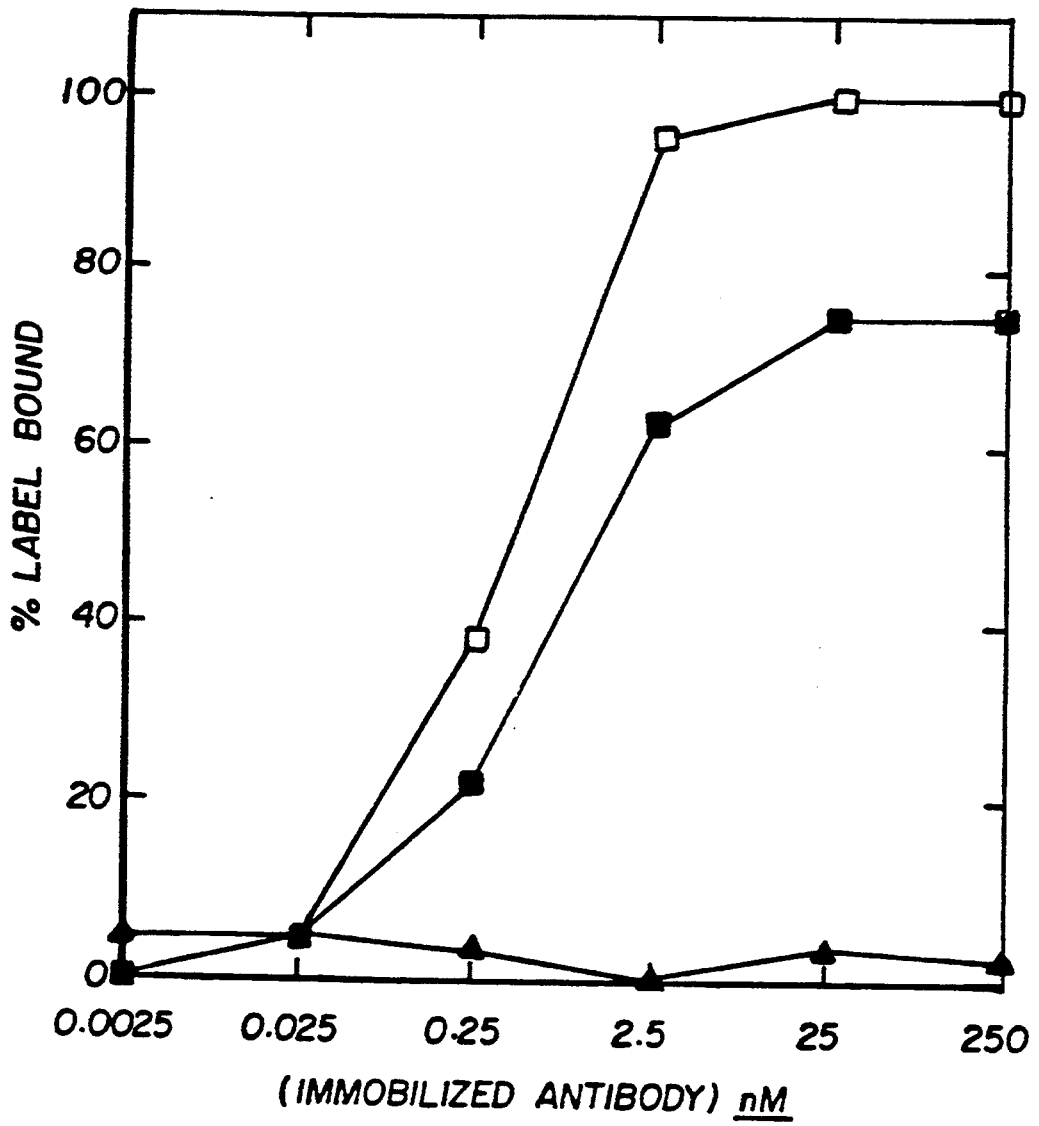
FIG. 1 illustrates the immunocompetency of amine-enriched HRP and HRP labeled ligand analogs containing oxidized digoxin product prepared according to the present invention.

The combination of periodic acid and chromium trioxide has been utilized for the selective oxidation of compounds having vicinal diols to carboxylic acids in the presence of other primary and secondary alcohols and ketones. Oxidation does not occur at any sites other than at the vicinal diol sites with this reagent system. Therapeutically useful steroids such as digoxin, digitoxin and ouabain have vicinal diols in their terminal saccharide ring.

Mono- and polysaccharides, including mono- and trisaccharides, containing asteroid or other biologically useful group, e.g., an immunologically reactive group, are oxidized at the vicinal diol sites in the terminal saccharide by a mixture of periodic acid and chromium trioxide in aqueous dioxane to give carboxylic acid derivatives. The mixture of periodic acid and chromium dioxide has a molar concentration ratio in the range 4/1 to 1/1, preferably 2/1.

The oxidation step involved in the the method can be carried out in any aqueous mixture comprising any miscible organic solvent such as dioxane, methanol, DMF, ethanol, propanol, isopropanol, acetone, etc. Dioxane, acetone and DMF are preferred.

The polysaccharide chain can be linear or branched as is known in the art as long as the linkage that unites the monosaccharide units is a glycosidic bond. This bond can be α or β, and can join the reactive units through linkages that are 1,2, 1,3, 1,4 or 1,6 in the linear sequence, or between those units that are at branch points in the polymer (*Principles of Biochemistry*, A. White et al, 6th Ed., McGraw-Hill, Inc. New York, N.Y., page 33). Although the saccharide units which make up the polymer are generally derived from D-glucose, they can be derived from other monosaccharides which are known to have substituents including lower alkyl, hydroxy, hydroxymethyl, lower alkoxy, lower acyloxy, and lower alkanamido, exemplary units being those derived from D-mannose, D- and L-galactose, D-xylose and L-arabinose. Other units also occur as constituents of polysaccharides such as D-glucuronic, D-galacturonic and D-mannuronic acids. A great many polysaccharides have been described, thus many variants are possible.

Exemplary saccharides such as the steroids digoxin, digitoxin and ouabain were oxidized by the above method to give mixtures containing mono- and dicarboxylic acids:

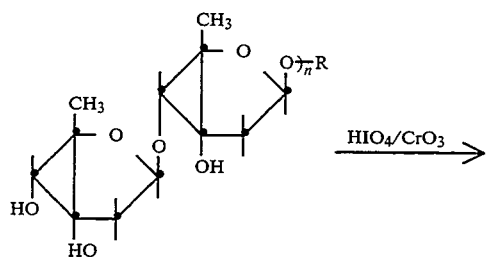

$\xrightarrow{HIO_4/CrO_3}$

-continued

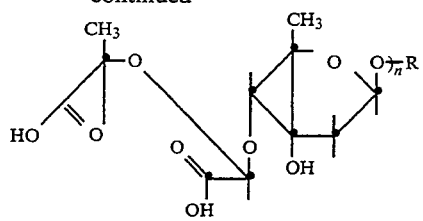

The immunologically reactive group R cannot contain vicinal diol groups, carboxylic acid groups (or equivalents thereof), primary amine, or sulfhydryl groups, as many immunologically reactive agents do, because vicinal diol groups would participate undesirably in the oxidation of step 2. The other named groups would participate in other unwanted condensation reactions, including self-crosslinking, in subsequent derivatizing (condensation) reactions used to append useful groups, such as labels or supports via the carboxyl groups.

Examples of useful R groups include haptens, residues of hormones, vitamins, alkaloids, lipids and steroids (including steroid residues of digoxin, digitoxin and ouabain) and other mono- or polysaccharides. R can be a component of physiological fluids, cell and tissue extracts, or a chemical compound that is capable of participating in an immunological reaction with a corresponding receptor compound (natural or synthetic). The receptor is a chemical or biological compound that has a reactive site for immunological reaction with R, the immunologically reactive group. By immunologically reactive group is meant any group that participates in an antigen-antibody reaction.

Although the R groups are "immunologically reactive" groups, saccharide groups can also function as immunologically reactive species. Therefore, for some uses the immunological activity of the R groups is predominant, for other uses the immunological activity of the saccharide groups is predominant, and in yet other uses, the immunological activity of both groups is desired. In the cases of digoxin and digitoxin assays, the latter situation wherein the immunological reactivity is derived from the combination of the steroid and saccharide groups, is preferred.

Useful labeled ligand analogs, within the ambit of Structure I, are represented by Structures Ia and Ib:

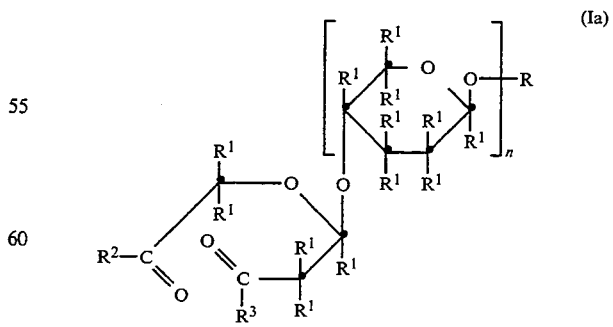

(Ia)

R, $R^2$, $R^3$ and n are each as defined in claim 2, and $R^1$, each independently, is hydrogen, lower alkyl, lower alkoxy, lower acyloxy, lower alkanamido, hydroxy or hydroxymethyl.

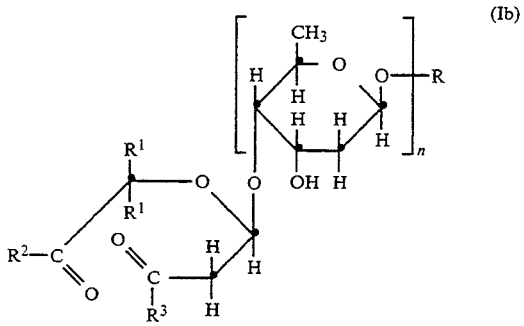

(Ib)

R, R¹, R² and R³ are as defined for structure Ia and n is 0 to 3.

The label, represented by the R² and/or R³ facilitates detection of the ligand analogs of Structures I, Ia and Ib. The label can itself be detectable such as a visible or fluorescent dye moiety or a radioactive substance. The label can be a group that can be rendered detectable by subsequent reactions, for example, leuco dye can be rendered visible by treatment with acid or base. The label can be an intermediate or catalyst that allows generation of a separate detectable species. For example, an enzyme label that catalyzes generation of peroxide with subsequent oxidation of leuco dye by the peroxide to produce a visible dye.

The label or support can be appended to a linking group [see step (c) of the method for making the labeled ligands] or can be chemically added to the linking groups while retaining a terminal amino or sulfhydryl group on the linking group to combine with the acid group(s) of Structure I to form the requisite amide or thioester group(s).

The linking group can be a support or substrate such as a polymeric bead, fiber, thin coating or sheet appended to the dicarboxylic acid product or a derivative.

One particularly useful support or supporting polymeric linking group is a polymer particle of addition-polymerizable vinyl (including acrylic) monomers.

The polymeric particles are generally water-insoluble latex particles having an average particle size greater than about 0.01 micrometers. Preferably they have an average particle size in the range of from about 0.01 to about 10, preferably about 0.3 to 3 micrometers.

Preferred polymers can be represented by the formula (II):
wherein —A—represents recurring units derived from one or more hydrophobic ethylenically unsaturated monomers,
—B—represents recurring units derived from one or more ethylenically unsaturated monomers having the requisite reactive groups through which the polymer particle can be appended to form ligand analogs;
—D—represents recurring units derived from one or more ethylenically unsaturated monomers which are different than those represented by —A—or —B—.

In formula (III), x is from 0 to about 99.9 mole percent, y is from about 0.1 to 100 mole percent and z is from 0 to 20 mole percent. Preferably, x is from about 45 to about 99.5 mole percent, y is from 0.5 to about 50 mole percent, and z is from 0 to about 10 mole percent. Polymer beads according to formula III are disclosed in EPA 0 308 233 A; 0 323 692 A; 0 280 556 A; and 0 302 715 A and Kokai 89/0054258 and 89/0054259, each of which are expressly incorporated herein by reference.

Monomers from which the —A—recurring units are selected are hydrophobic and form homopolymers that are insoluble in water. Preferably, these monomers have aromatic groups. Representative hydrophobic monomers include, but are not limited to, styrene and styrene derivatives (for example, 4-vinyltoluene, 2,5-di-methylstyrene, 4-t-butylstyrene, 2-chlorostyrene and others known in the art), acrylic and methacrylic acid esters and amides (for example, n-butyl acrylate, propyl methacrylate, methyl acrylate, methyl methacrylate, ethyl methacrylate, 2-ethylhexyl methacrylate, N-phenylacrylamide and others known in the art), acrylonitrile and vinyl acetate.

The monomers from which the —B—recurring units are selected are vinylbenzyl chloride, vinylbenzyl bromide, m- and p-(2-chloroethylsulfonylmethyl)styrene, N-(4-chloroethylsulfonylmethylphenyl)acrylamide, vinyl chloroacetate, N-(3-chloroacetamidopropyl)methacrylamide, 2-chloroacetamidoethyl methacrylate, 4-chloroacetamidostyrene, m- and p-chloracetamidomethylstyrene, N-(3-chloroacetamidocarbonyliminopropyl)methacrylamide, 2-chloroacetamidocarbonyliminoethyl methacrylate, 4-chloroacetamidocarbonyliminostyrene, m- and p-chloroacetamidocarbonyliminomethylstyrene, N-vinyl-N'-(3-chloropropionyl)urea, 4,(3-chloropropionamido)styrene, 4-(3-chloropropionamidocarbonylimino)styrene, 2-(3-chloropropionamido)ethyl methacrylate, N-[2-(3-chloropropionamido)ethyl]methacrylamide, acrylic acid, methacrylic acid, glycidyl acrylate, glycidyl methacrylate, vinylbenzaldehyde and N-(3-aminopropyl)methacrylamide hydrochloride.

Monomers from which the —D—recurring units are derived include monomers different than those from which —A—and —B—are derived. Specifically, the —D—recurring units are derived from monomers which impart aqueous dispersion stability to the particles or other properties. Representative monomers include, but are not limited to, anionic monomers such as sodium 2-acrylamido-2-methylpropanesulfonate, acrylic acid, methacrylic acid, 2-carboxyethyl acrylate, styrene sulfonic acid, potassium salt and m & p-carboxymethylstyrene and other ethylenically unsaturated polymerizable sulfonates, carboxylates, sulfates and phosphonates, other hydrophilic but nonionic monomers, such as 2-hydroxyethyl acrylate and 2-hydroxyethyl methacrylate and others known to one skilled in the art.

Preferred monomers from which the —D—units are derived are acrylic acid, methacrylic acid, sodium 2-acrylamido-2-methylpropanesulfonate, m & p-carboxymethylstyrene and p-styrenesulfonic acid, potassium salt.

Representative polymers of the monomers described above include the following: poly(m & p-chloromethylstyrene), poly(styrene-co-m & p-chloromethylstyrene-co-2-hydroxyethyl acrylate) (67:30:3 molar ratio), poly(styrene-co-m & p-chloroethylsulfonylmethylstyrene) (95.5:4.5 molar ratio), poly{styrene-co-N-[m & p-(2-chloroethylsulfonylmethyl)phenyl]acrylamide}(99.3:0.7 molar ratio), poly(m & p-chloromethylstyrene-co-methacrylic acid)(95:5, 98:2 and 99.8:0.2 molar ratio), poly(styrene-co-m & p-chloroethylsulfonylmethyl-styrene-co-methacrylic acid)(93.5:4.5:2 molar ratio), poly{styrene-co-N-[m & p-(2-chloroethylsulfonylmethyl)phenyl]acrylamide-co-methacrylic acid}(97.3:0.7:2 molar ratio), and poly(- styreneco-m & p-chloromethylstyrene)(70:30 molar ratio).

The polymer beads can be bonded to the carboxylic acid oxidation products of the invention only when the bead contains a group which reacts with the carboxylic acid groups (or equivalents thereof), i.e., amine or sulfhydryl groups. Alternatively, however, an auxiliary crosslinking agent can be employed to introduce amine or sulfhydryl groups to the polymer bead to allow subsequent attachment to the dicarboxylic acid oxidation product. For this purpose, known crosslinking agents such as diamines, biomercaptans, and the like can be used. Attachment of polymers to the dicarboxylic acid oxidation products can also be facilitated by use of crosslinking agents which do not necessarily introduce additional linking groups. Examples of such crosslinking agents are carbodiimides and carbamoylonium compounds as mentioned in U.S. Pat. No. 4,421,847.

In addition, the dicarboxylic oxidation products can be attached to a polymer such as a protein which is then appended to beads as described above whereby the protein serves as a large linking group between oxidation product and the bead. The protein can serve other purposes such as improving aqueous and/or biological compatibility, as well as extending the immunologically reactive group away from the polymer particle.

The ligand analogs of this invention are useful in any immunoassay that employs ligand analogs, whether labeled or on a support. The assay may be competitive as described supra, homogenous or heterogenous as those terms are understood in the art. See, for example U.S. Pat. No. 4,670,381. The assay may be direct or indirect. ELISA, EMIT and FIA are well known examples of such immunoassays.

In one embodiment an immunoassay is provided for a ligand comprising the steps of:
(a) providing a ligand analog according to the invention attached to a support;
(b) providing a receptor, having a detectable label attached thereto, for the ligand and the ligand analog;
(c) mixing (a) and (b); and
(d) measuring the bound or unbound labeled receptor.

In another embodiment an immunoassay is provided for a ligand comprising the steps of:
(a) providing a labeled ligand analog according to the invention;
(b) mixing the ligand with (a);
(c) reacting the mixture from (b) with a known amount of an antibody for the ligand, and
(d) measuring the amount of labeled ligand analog.

The labeled ligand analogs of Structure I are useful in dry analytical elements designed to carry out immunoassays. Such elements typically comprise support layer, a reagent zone, and a spreading zone. The two zones can be combined into a single layer or can be separate layers. The element can comprise one or more layers, e.g. separate or combined reagent/spreading layer and a gelatin buffer layer containing other necessary additives, coupling enzymes, etc. The beads, can include both large and small polymeric beads, and they can either be coated in the same or different layers. The small beads can be coated before, concurrently with or after the large beads.

The reagent layer or the spreading layer of the element can contain the indicator composition comprising one or more reagents dispersed in one or more synthetic or natural binder materials, such as gelatin, or other naturally-occurring colloids, homopolymers and copolymers, such as poly(acrylamide), poly(vinyl pyrrolidone), poly(N-isopropylacrylamide), poly(acrylamide-co-N-vinyl-2-pyrrolidone) and similar copolymers.

Other optional layers, e.g. subbing layers, radiation-blocking layers, etc. can be included if desired. All layers of the element are in fluid contact with each other, meaning that fluids and reagents and uncomplexed reaction products in the fluids can pass between superposed regions of adjacent layers.

The various immunoassays provided by this invention assay can be carried out using any suitable label which can be attached to the dicarboxylic acid product. Useful labels include radioactive tags, dyes, fluorescers, enzymes, enzyme substrates, enzyme inhibitors, allosteric effectors, cofactors and other known enzyme modulators. Enzymes, such as glucose oxidase, peroxidase, alkaline phosphatase, horseradish peroxidase, including amine-enriched horseradish peroxidase, and galactosidase are preferred labels.

When an enzyme label is used, the substrate for the enzyme is present in the element or added thereto in the wash liquid. The substrate can be added to the element prior to or simultaneously with the liquid sample, or after completion of the binding reaction. It is within the skill of the ordinary worker in clinical chemistry to determine a suitable substrate for a given label. The substrate can be a material which is directly acted upon by the enzyme label, or a material that is involved in a series of reactions which involve enzymatic reaction of the label. For example, if the enzyme label is peroxidase, the substrate is hydrogen peroxide. Using glucose oxidase as an example, the substrate glucose is generally present in the reagent layer or added in the wash liquid to yield about 0.01 moles/m$^2$, and preferably from about 0.001 to about 0.1 mole/m$^2$. A worker skilled in the art would know how to adjust the amount of a particular substrate for the amount of enzyme label used in the assay.

If a labeled ligand analog of Structure I is not incorporated in the element during manufacture, it can be mixed with the test sample simultaneously with or prior to contact with the element.

When certain labels are used, e.g. enzymes, cofactors, enzyme substrates or enzyme modulators, the reagent layer contains an indicator composition comprising one or more reagents which provide a detectable species as a result of reaction of the label. Preferably, the indicator composition is a colorimetric indicator composition which provides a colorimetrically detectable species as a result of enzymatic reaction of an enzyme-labeled ligand analog with a substrate.

The indicator composition can be a single compound which produces a detectable dye upon enzymatic reaction, or a combination of reagents which produce the dye. For example, when glucose is used as the substrate and glucose oxidase as the enzyme label, the colorimetric indicator composition can include a coupler and oxidizable compound which react to provide a dye. Alternatively, the composition can include a leuco dye and peroxidase or another suitable peroxidative compound which generates a detectable dye as a result of the formation of hydrogen peroxide produced when glucose oxidase converts glucose to gluconic acid. Useful leuco dyes are known in the art and include those, for example, described in U.S. Pat. No. 4,089,747 (issued May 16, 1978 to Bruschi) and U.S. Ser. No.

612,509, filed May 21, 1984 by Babb et al. The particular amounts of the colorimetric indicator composition and its various components are within the skill of a worker in the art.

The layers of the element can contain a variety of other desirable but optional components, including surfactants, thickeners, buffers, hardeners, antioxidants, coupler solvents, and other materials known in the art. The amounts of these components are also within the skill of a worker in the art.

The immunoassay can be manual or automated. In general, the amount of analyte in a liquid sample is determined by taking the element from a supply roll, chip packet or other source and physically contacting a finite area of the spreading layer with a sample of the liquid, e.g. 1 to 100 μl. The finite area which is contacted is generally no more than about 100 mm$^2$.

After sample application in either embodiment, the element is exposed to any conditioning, such as incubation, heating or the like, that may be desirable to quicken or otherwise facilitate obtaining the test result.

The amount of analyte is determined by passing the element through a suitable apparatus for detecting the complexed ligand analog directly or the detectable species formed as a result of enzymatic reaction of an enzyme label and a substrate. For example, the species can be detected with suitable radiometric, fluorometric or spectrophotometric apparatus using generally known procedures. In an enzymatic reaction, the resulting product is determined by measuring, for example, the reflection or transmission density or fluorescence in the center of the finite area which was contacted with the test sample. The area which is measured is generally from about 3 to about 5 mm in diameter for competing assays. The amount of analyte in the liquid sample is inversely proportional to the amount of label measured in the center of the finite area. As mentioned hereinbefore, in a preferred embodiment a separate wash step is required in order to separate complexed ligand from uncomplexed ligand (radial wash). Generally, label measurement is carried out after from about 5 to about 180 seconds after sample contact and spreading or application of the wash liquid.

The following examples 1-3 illustrates the method of making the dicarboxylic acid products used in making the ligand analogs of structure I.

EXAMPLE 1

Preparation of the Dicarboxylic Acid Oxidation Product of Digoxin

Periodic acid (6.84 g, 30.0 mmol) and chromium trioxide (1.50 g, 15.0 mmol) were added simultaneously to a slurry of digoxin (2.00 g, 2.56 mmol) in 150 mL of 50% aqueous dioxane cooled to 0° C. The resulting solution was stirred 1 hour at 0° C. The reaction mixture was poured into 500 mL of water. The products were extracted with ethyl acetate (3×75 mL). The combined organic extracts were washed with brine (3×100 mL), dried over sodium sulfate and concentrated. The residue was dissolved in 20 mL of hot ethyl acetate and then diluted with ether at ambient temperature until the solution became cloudy. Chilling precipitated a white powder which was collected by filtration, washed with ether, and dried to give oxidized digoxin product. Yield 1.68 g (81%), mp 152°-155° C.: $^1$H NMR (D$_2$O, CDCl$_3$) δ 5.95 (s, 1 H), 5.2–4.6 (m, 7 H), 4.3–3.7 (m, 5 H), 3.55 (m, 2 H), 3.30 (m, 1 H), 2.9–2.6 (m, 4 H), 2.5–2.1 (m, 2 H), 2.1–1.5 (m, 11 H), 1.5–1.1 (m, 16 H), 1.03 (s, 3H), 1.00 (s, 3 H); $^{13}$C NMR (CDCl$_3$) δ 212.2, 205.4, 203.8, 202.3,201.8, 175.3,175.1, 174.4, 118.2, 100.3, 99.6, 99.5, 98.3, 86.5, 86.44, 84.3, 84.1, 78.1, 77.7, 74.0, 73.7, 73.6, 73.0, 71.2, 71.1, 64.1, 48.9, 46.2, 41.1, 39.8, 37.3, 36.4, 35.4, 33.4, 32.7, 29.9, 29.85, 29.8, 26.9, 26.3, 26.2, 26.15, 26.1, 23.2, 21.8, 18.9, 18.6, 18.6, 18.55, 18.53, 18.45, 16.5, 15.1.

EXAMPLE 2

Preparation of the Dicarboxylic Acid Oxidation Product of Digitoxin

Periodic acid (6.84 g, 30.0 mmol) and chromium trioxide (1.50 g, 15.0 mmol) were added simultaneously to a slurry of digitoxin (2.00 g, 2.61 mmol) in 150 mL of 50% aqueous dioxane cooled to 0° C. The resulting solution was stirred 1 hour at 0° C and then allowed to warm to ambient temperature. The solution was poured into 500 mL of water. The product was extracted with ethyl acetate (3×75 mL). The combined organic extracts were washed with brine (3×100 mL), dried over sodium sulfate, and concentrated. The residue was dissolved in 20 mL of hot ethyl acetate and then diluted with pentane at ambient temperature until the solution became cloudy. Chilling precipitated a white powder which was collected by filtration, washed with pentane and dried to give 1.55 g (75%) of oxidized digitoxin product. MP 135°-145° C.: $^1$H NMR (CDCl$_3$) δ 5.90 (s, 1H), 5.18 (m, 1 H), 5.01 (d, 1 H), 4.98 (br s, 1 H), 4.83 (br s, 1 H), 4.81 (d, 1 H), 4.79 (m, 1 H), 4.50 (br, 5 H), 4.23 ( d, 1 H), 4.10 (br s, 1 H), 3.96 (d, 1 H), 3.64 (m, 1 H), 3.58 (m, 1 H), 2.78 (m, 6 H), 2.15 (m, 2 H), 1.87 (m, 2 H), 1.8–1.3 (m, 19 H), 1.25 (m, 9 H), 0.95 (s, 3 H), 0.90 (s, 3 H).

EXAMPLE 3

Preparation of the Dicarboxylic Acid Oxidation Product of Ouabain

Periodic acid (4.56 g, 20.0 mmol) and chromium trioxide (1.00 g, 10.0 mmol) were added simultaneously to a stirred slurry of ouabain (1.00 g, 1.37 mmol) in 50 mL of 50% aqueous dioxane cooled to 0° C. The resulting solution was stirred 1 hour at 0° C. and then allowed to warm to ambient temperature. The reaction mixture was poured into 200 mL of water. The products were extracted with ethyl acetate (3×50 mL). The combined organic extracts were washed with brine (5×50 ml) until colorless, dried over sodium sulfate, and concentrated. The residue was dissolved in 5 mL of hot ethyl acetate and diluted with ether at ambient temperature until the solution became cloudy. Chilling precipitated a white powder which was collected by filtration, washed with ether, and dried yield 0.13 g (13%), mp 135°-139° C.

The following examples 4-8 illustrate a method for preparing labeled ligand analogs according to the invention.

EXAMPLE 4

Preparation of Amine-Enriched Horseradish Peroxidase (HRP) Labeled Digoxin Analog The oxidized digoxin product of Example 1 (102 mg, 1.25×10$^{-4}$ mol) was dissolved in 2.5 mL of dry N,N-dimethylformamide (DMF). Tributylamine (23 μL, 1.25×10$^{-4}$ mol) was added and the resulting solution was cooled in an ice bath. Isobutyl chloroformate (17.1

μL, 1.25×10$^{-4}$ mol) was added and the resulting solution was stirred for 20 minutes at 0° C.

An improved amine enriched HRP was prepared as follows. HRP (200 mg) was dissolved in 40 mL of deionized distilled water. Ten mL of freshly made 0.1M sodium periodate in water was added and the resulting solution was stirred in the dark for 20 minutes. The reaction mixture was dialyzed overnight against 0.001M sodium acetate buffer (pH 4.0). Lysyl-lysine bishydrochloride salt (0.868 g, 12.5 mmol) was dissolved in 50 mL of 0.1M sodium carbonate (pH 9.5). The oxidized HRP solution was added and the resulting solution was stirred for 1 hour at ambient temperature. The pH was lowered to 8.0 and sodium cyanoborohydride (100 mg) was added. Stirring was continued for 3 hours. Glycine (1.5 g) and an additional 100 mg of sodium cyanoborohydride were added with stirring for an additional 3 to 4 hours. The reaction mixture was dialyzed against 0.02M 3-N-morpholinopropane sulfonic acid (MOPS, pH 7.0) changing the dialysis buffer twice over a 14 hour period. The amine-enriched HRP was purified by size exclusion chromatography when necessary to remove any HRP aggregates. Merthiolate (0.02%) was added as a preservative.

Deionized distilled water was added to 50 mg (1.25×10$^{-6}$ mol) of the amine-enriched HRP to a volume of 25 mL. The pH of this solution was adjusted to 9.0 with dilute sodium hydroxide solution. The solution containing the oxidized digoxin product was added dropwise to the solution containing the amine-enriched HRP while the pH was maintained at 9.0. After addition was complete, stirring at pH 9 was continued for 1.5 hours, and then the pH was lowered to 7.0 with dilute hydrochloric acid. Hydroxylamine was added to a final concentration of 0.020M and the resulting solution was stirred for 2 hours. The reaction mixture was dialyzed against 3 L of 0.02M MOPS, pH 7.00, overnight with the dialysis buffer being changed once during this period. The label was purified by gel filtration (Bio-Gel P-2, 200–400 mesh) eluting with 0.02 M MOPS, pH 7.0. Merthiolate (0.01%) was added as a preservative.

EXAMPLE 5

Preparation of HRP Labeled Ligand Digoxin Analog

The oxidized digoxin product of Example 1 (102 mg, 1.25×10$^{-4}$ mol) was dissolved in 2.5 mL of dry N,N-dimethylformamide (DMF). Tributylamine (23 μL, 1.25×10$^{-4}$ mol) was added and the resulting solution was cooled in an ice bath. Isobutyl chloroformate (17.1 μL, 1.25×10$^{-4}$ mol) was added and the resulting solution was stirred for 20 minutes at 0° C.

Deionized distilled water was added to 50 mg (1.25×10$^{-6}$ mol) of HRP to a volume of 25 mL. The pH of this solution was adjusted to 9.0 with dilute sodium hydroxide solution. The solution containing the oxidized digoxin was added dropwise to the solution containing amine-enriched HRP as in Example 4, while the pH was maintained at 9.0. After addition was complete, stirring at pH 9 was continued for 1.5 hours, and then the pH was lowered to 7.0 with dilute hydrochloric acid. Hydroxylamine was added to a final concentration of 0.020M and the resulting solution was stirred for 2 hours. The reaction mixture was dialyzed against 3 L of 0.02M MOPS, pH 7.0, overnight with the dialysis buffer being changed once during this period. The label was purified by gel filtration (Bio-Gel P-2, 200–400 mesh) eluting with 0.02 M MOPS, pH 7.0. Merthiolate (0.01%) was added as a preservative.

EXAMPLE 6

Preparation of Amine-Enriched HRP Labeled Digitoxin Analog

The oxidized digitoxin product of Example 2 (100 mg, 1.25×10$^{-4}$M) was dissolved in 2.5 mL of dry N,N-dimethylformamide (DMF). Tributylamine (23 μL, 1.25×10$^{-4}$ mol) was added and the resulting solution was cooled in an ice bath. Isobutyl chloroformate (17.1 μL, 1.25×10$^{-4}$ mol) was added and the resulting solution was stirred for 20 minutes at 0° C.

Deionized distilled water was added to 50 mg (1.25×10$^{-6}$ mol) of the amine-enriched HRP to a volume of 25 mL. The pH of this solution was adjusted to 9.0 with dilute sodium hydroxide solution. The solution containing the oxidized digitoxin product was added dropwise to the solution containing the amine-enriched HRP while the pH was maintained at 9.0. After addition was complete, stirring at pH 9 was continued for 1.5 hours, and then the pH was lowered to 7.0 with dilute hydrochloric acid. Hydroxylamine was added to a final concentration of 0.020M and the resulting solution was stirred for 2 hours. The reaction mixture was dialyzed against 3L of 0.02M MOPS, pH 7.00, overnight with the dialysis buffer being changed once during this period. The label was purified by gel filtration (Bio-Gel P-2, 200–400 mesh) eluting with 0.02M MOPS, pH 7.0. Merthiolate (0.01%) was added as a preservative.

EXAMPLE 7

Preparation of Alkaline Phosphatase (ALP) Labeled Digoxin Analog

The oxidized digoxin product of Example 1 (20.3 mg, 2.5×10$^{-5}$ mol) was dissolved in 2.5 mL of dry N,N-dimethylformamide (DMF). Tributylamine (4.6 μL, 2.5×10$^{-5}$ mol) was added and the resulting solution was cooled in an ice bath. Isobutyl chloroformate (3.42 μL, 2.5×10$^{-5}$ mol) was added and the resulting solution was stirred for 20 minutes at 0° C.

Deionized distilled water was added to 25 mg (2.5×10$^{-7}$ mol) of ALP to a volume of 25 mL. The pH of this solution was adjusted to 9.0 with dilute sodium hydroxide solution. The solution containing the oxidized digoxin product was added dropwise to the solution containing the ALP while the pH was maintained at 9.0. After addition was complete, stirring at pH 9.0 was continued for 1.5 hours, and then the pH was lowered to 7.0 with dilute hydrochloric acid. Hydroxylamine was added to a final concentration of 0.020M and the resulting solution was stirred for 2 hours. The reaction mixture was dialyzed against 3L of phosphate buffered saline (PBS) overnight with the dialysis buffer being changed once during this period. The label was purified by gel filtration (Bio-Gel P-2, 200–400 mesh) eluting with PBS. The protein containing fractions were dialyzed against 0.05M tris(hydroxymethyl)aminomethane (TRIS), pH 8.0, containing 0.001M magnesium chloride and 0.0001M zinc chloride. The dialysis buffer was changed once. Sodium azide (0.02%) was added as a preservative and the label was stored in the dark at 4° C.

EXAMPLE 8

Preparation ALP Labeled Digitoxin Analog

The oxidized digitoxin product of Example 2 (19.9 mg, $2.5 \times 10^{-5}$ mol) was dissolved in 2.5 mL of dry N,N-dimethylformamide (DMF). Tributylamine (4.6 µL, $2.5 \times 10^{-5}$ mol) was added and the resulting solution was cooled in an ice bath. Isobutyl chloroformate (3.42 µL, $2.5 \times 10^{-5}$ mol) was added and the resulting solution was stirred for 20 minutes at 0° C.

Deionized distilled water was added to 25 mg ($2.5 \times 10^{-7}$ mol) of ALP to a volume of 25 mL. The pH of this solution was adjusted to 9.0 with dilute sodium hydroxide solution. The solution containing the oxidized digitoxin was added dropwise to the solution containing the ALP while the pH was maintained at 9.0. After addition was complete, stirring at pH 9.0 was continued for 1.5 hours, and then the pH was lowered to 7.0 with dilute hydrochloric acid. Hydroxylamine was added to a final concentration of 0.020M and the resulting solution was stirred for 2 hours. The reaction mixture was dialyzed against 3 L of phosphate buffered saline (PBS) overnight with the dialysis buffer being changed once during this period. The label was purified by gel filtration (Bio-Gel P-2, 200–400 mesh) eluting with phosphate buffered saline, the protein containing fractions were dialyzed against 0.05M tris(hydroxymethyl)aminomethane (TRIS), pH 8.0, containing 0.001M magnesium chloride and 0.0001M zinc chloride. The dialysis buffer was changed once. Sodium azide (0.02%) was added as a preservative and the label was stored in the dark at 4° C.

EXAMPLES 9–10

The following procedure was used to test the immunocompetency of exemplary enzyme labeled ligand analogs of Structure I prepared in Examples 4–5.

Polymer beads coated with immobilized digoxin antibody in PBS containing 1.0% bovine serum albumin (BSA) were placed at various dilutions (so that the final concentration of immobilized antibody was between 0.0025 and 250 nM) into wells (50 µL samples) of a V-bottom, 96-well microtiter plate. A Structure I enzyme label prepared in one of Examples 4–5 (50 µL) was then added and followed by an additional 50 µL of the PBS/BSA buffer.

A control enzyme label prepared from sodium periodate oxidation of digoxin followed by reaction with HRP was treated in the same manner. The final concentration of each HRP label was $5 \times 10^{-11}$M.

The final concentration of each of the HRP labels was $5 \times 10^{-11}$M.

The wells for the control label and the Structure I label were covered and placed in a shaker for 1 hour. The wells were then centrifuged at 2500 RPM. Three 25 µL aliquots of the supernatant were removed from each well and were placed in the wells of a flat-bottom plate. A 75 µL aliquot of an HRP detection reagent (prepared from a leuco dye, hydrogen peroxide and an electron transfer agent) was then added. The rate of appearance of dye density was then monitored spectrophotometrically.

FIG. 1 shows the result of the foregoing test for amine-enriched HRP and HRP labeled ligand analogs comprising oxidized digoxin product according to the invention compared to the control. Immunoreactivity testing of the enzyme labels prepared from oxidized digoxin labeled with amine-enriched HRP from Example 4 (open squares) and with HRP Example 5 (filled squares). These data can be compared with the control (filled triangles). The data of FIG. 1 shows that labels prepared from the oxidized digoxin diacid attached directly to HRP and amine-enriched HRP were 75% and 100% bound by antibody, respectively.

As shown in FIG. 1, the control, prepared from the sodium periodate oxidation of digoxin to a dialdehyde followed by linkage to HRP through the enzyme's amines, performs poorly in immunocompetency tests. More than 90% of the enzyme remains unbound. The labels prepared by this invention represent significant improvements in immunoassay of digoxin.

An exemplary multilayer dry immunoassay element format is disclosed in U.S. Application Ser. No. 444,079 filed Nov. 30, 1989 entitled "Dry Immunoassay Analytical Element Comprising Monodispersed Beads" by L. A. Mauck et al, which employ monodisperse polymer beads of two different sizes coated either in separate layers or in admixture in a single layer. This format is used in Example 11, infra.

EXAMPLE 11

Coated Thin Film Immunoassay for Digoxin

This example illustrates a competitive immunoassay for digoxin using a multilayer thin-film format and a separate wash step. The label was prepared essentially as described in Example 4. The structure of the element was:

| Element Structure for Digoxin | |
|---|---|
| | Coverage (g/m²) Preferred |
| Spreading Layer: | |
| Large Beads, 30 µm | 130 |
| Small Beads with Antibodies 0.5 µm | 0.02 |
| Triarylimidazole Leuco Dye | 0.2 |
| Dimethyl sulfoxide | 1.8 |
| Binder | 2.6 |
| *TES Buffer, pH 7.0 | 0.2 |
| **Kelzan | 0.07 |
| 5,5-Dimethyl-1,3-cyclohexanedione | 0.05 |
| Surfactant Zonyl FSN (duPont) | 0.05 |
| Surfactant 10G (Olin Chem. Co.) | 0.24 |
| Gelatin Layer: | |
| Hardened Gelatin | 10 |
| 4'-Hydroxyacetanilide | 0.15 |
| *TES Buffer, pH 7.0 | 4.6 |
| Surfactant TX-100 | 0.02 |
| SUPPORT | |

*TES is N-[tris(hydroxymethyl)methyl]-2-amino-ethanesulfonic acid.
**Kelzan is a xanthan gum sold by Kelco and serves as an emulsion stabilizer.

A stock solution of the digoxin-HRP label ligand analog was prepared in 0.2M MOPS, pH 7.0, containing bovine serum albumin (1%), 0.01M 4'-hydroxyacetanilide and 0.02% merthiolate. A sample of the above stock solution of digoxin-HRP (0.1 ml) was combined with a series of digoxin standards (0.9 ml) which were prepared by adding digoxin to a delipidized human serum matrix.

Ten microliter aliquots were spotted onto the digoxin element. After 5 minutes at 37° C., a wash solution (10 µL) containing hydrogen peroxide was added to wash unbound digoxin-HRP away from the center of the element. After 40 seconds, the change in reflectance density (ΔDr) was measured for 30 seconds in the center of the element at 37° C. and 680 nm. The Williams- Clapper transform [J. Opt. Soc. Am., 43, 595 (1953)] was used to convert the reflection densities to transmittance values (ΔDt).

The results are shown below:

| Digoxin concentration (ng/mL) | Rate (ΔDt/min.) |
|---|---|
| 0.00 | 0.056 |
| 0.06 | 0.057 |
| 0.53 | 0.055 |
| 1.05 | 0.053 |
| 1.52 | 0.049 |
| 1.96 | 0.046 |
| 3.03 | 0.042 |
| 4.30 | 0.032 |
| 4.30 | 0.031 |
| 6.23 | 0.028 |

These results show that the digoxin-HRP label prepared according to the method of the invention performs well in a coated digoxin assay multilayer dry analytical element.

The invention has been described in detail with particular reference to preferred embodiments thereof, but it will be understood that variations and modifications can be effected within the spirit and scope of the invention.

We claim:

1. A method of making a ligand analog comprising a dicarboxylic acid oxidation product of a immunologically reactive monosaccharide or polysaccharide having vicinal diols, to which a label or a support is appended through an amide or thioester linkage, comprising the steps of:

(a) providing a monosaccharide or polysaccharide having i) a group capable of specific binding with an immunologically reactive analyte and ii) two vicinal diols located on a terminal saccharide group;

(b) oxidizing the terminal saccharide group at the vicinal diols with a mixture of periodic acid and chromium trioxide in an aqueous solution of a water-miscible organic solvent mixture, to produce the dicarboxylic acid product; and (c) condensing the dicarboxylic acid product with a label or support containing an amino or sulfhydryl group.

2. The method of claim 1 wherein the mixture of periodic acid and chromium trioxide has a molar concentration ratio in the range of 4/1 to 1/1.

3. The method of claim 2 wherein the molar concentration ratio is 2/1.

4. The method of claim 2 or 3 wherein the label is an enzyme selected from the group consisting of horseradish peroxidase, amine-enriched horseradish peroxidase, and alkaline phosphatase.

5. A method according to claim 2 or 3 wherein the support is a polymer particle, fiber or film.

* * * * *